United States Patent
Burger et al.

(10) Patent No.: US 6,926,897 B1
(45) Date of Patent: Aug. 9, 2005

(54) MEDICAMENT FOR THE AVOIDANCE OR TREATMENT OF PAPILLOMAVIRUS-SPECIFIC TUMOUR

(75) Inventors: Alexander Burger, Munich (DE); Michael Hallek, Schondorf (DE)

(73) Assignee: MediGene Aktiengesellschaft, Martinsried (DE)

( * ) Notice: Subject to any disclaimer, the term of this patent is extended or adjusted under 35 U.S.C. 154(b) by 232 days.

(21) Appl. No.: 09/667,556

(22) Filed: Sep. 22, 2000

Related U.S. Application Data (63) Continuation of application No. PCT/EP99/01996, filed on Mar. 24, 1999.

(30) Foreign Application Priority Data

Mar. 24, 1998 (DE) .......................................... 198 12 941

(51) Int. Cl.⁷ ........................ A61K 39/00; A61K 39/12; C07K 17/00
(52) U.S. Cl. ............................... 424/192.1; 424/185.1; 424/204.1; 530/350
(58) Field of Search .......................... 424/185.1, 192.1, 424/196.11, 199.1, 202.1, 204.1; 530/300, 350

(56) References Cited

U.S. PATENT DOCUMENTS

| | | | |
|---|---|---|---|
| 5,618,536 A | 4/1997 | Lowy et al. ............. | 424/192.1 |
| 6,066,324 A | 5/2000 | Gissmann et al. ........ | 424/204.1 |
| 6,165,471 A | 12/2000 | Garcea et al. ........... | 424/186.1 |

FOREIGN PATENT DOCUMENTS

| | | |
|---|---|---|
| EP | 343 783 | 4/1989 |
| EP | 390 252 | 3/1990 |
| EP | A-0565794 | 8/1992 |
| WO | WO 93/20844 | 10/1933 |
| WO | WO 90/10459 | 9/1990 |
| WO | WO 93/00436 | 1/1993 |
| WO | WO 93/02184 | 2/1993 |
| WO | WO 93/21958 | 11/1993 |
| WO | WO 94/00152 | 1/1994 |
| WO | WO 94/05792 | 3/1994 |
| WO | WO 94/20137 | 9/1994 |
| WO | WO 96/00583 | 1/1996 |
| WO | WO 96/11272 | 4/1996 |
| WO | WO 96/11274 | 4/1996 |
| WO | WO 96/19496 | 6/1996 |
| WO | WO 98/04705 | 2/1998 |
| WO | WO 99/01557 | 1/1999 |
| WO | WO 94/23037 | 2/2000 |
| WO | WO 96/29091 | 8/2000 |

OTHER PUBLICATIONS

Muller et al. 1997. Chimeric Papillomavirus–like Particles. Virology. vol. 234, pp. 93–111.*

Hines et al. Feb. 1998. Prospects for human papillomavirus vacine development: emerging HPV vaccines. Current Opinion in Obstetrics and Gynecology. vol. 10, pp. 15–19.*

Karasuyama et al., "Establishment Of Mouse Lines Which Constitutively Secrete Large Quantities Of Interleukin 2, 3, 4 Or 5, Using Modified cDNA Expression Vectors", *Immunol.*, pp. 97–104, (1988).

G. Shaw et al., "Genetics", *A Conserved AU Sequence from the 3' Untranslated Region of GM–CSF mRNA Mediates Selective mRNA Degradation*, pp. 659–667 (1988).

M. Hagensee et al., "Journal of Virology", *Self–Assembly of Human Papillomavirus Type 1 Capsids by Expression of the L1 Protein Alone or by Coexpression of the L1 and L2 Capsid Proteins*, pp. 315–322 (1993).

Xi et al., "Journal of General Virology", *Baculovirus expression of the human papillomavirus type 16 capsid proteins: detection of L1–L2 protein complexes*, pp. 2981–2988 (1991).

R.C. Rose et al., "Journal of Virology", vol. 67, No. 4, *Expression of Human Papillomavirus Type 11 L1Protein in Insect Cells: In Vivo and In Vitro Assembly of Viruslike Particles*, pp. 1936–1944, (Apr. 1993).

J. Zhou et al., "Virology", vol. 185, *Expression of Vaccinia Recombinant HPV 16 L1 and L2 ORF Proteins in Epithelial Cells is Sufficient for Assembly of HPV Virion–like Particles*, pp. 251–257, (1991).

M. S. Barbosa et al., "Journal of Virology", vol. 65 No. 1, *In Vitro Biological Activities of the E6 and E7 Genes Vary among Human Papillomaviruses of Different Oncogenic Potential*, pp. 292–298, (Jan. 1991).

J.M. Arbeit et al., "Journal of Virology", vol. 68, *Progressive Squamous Epithelial neoplasia in K14–Human Papillomavirus Type 16 Transgenic Mice*, pp. 4358–4368, (Jul. 1994).

P. Kaur et al., "J. Gen. Virology", vol. 70, *Immortalization of Primary Human Epithelial Cells by Cloned Cervical Carcinoma DNA Containing Human Papillomavirus Tyep 16 E6/E7 Open Reading Frames*, pp. 1261–1266, (1989).

L. Gao et al., "Journal of General Virology", vol. 75, *Immune Response to Human Papillomavirus Type 16 E6 Gene in a Live Vaccinia Vector*, pp. 157–164, (1994).

(Continued)

Primary Examiner—James Housel
Assistant Examiner—Shanon Foley
(74) Attorney, Agent, or Firm—Foley & Lardner LLP (57) ABSTRACT

The invention relates to a medicament for preventing or treating human papilloma virus (HPV)-specific tumors containing at least one fusion protein and optional suitable additives and/or auxiliary agents. Said fusion protein is comprised of at least one L1-protein of one or more papilloma viruses, and is also comprised of at least one E-protein of one or more papilloma viruses, whereby the fusion protein does not contain any papilloma virus non-specific epitopes.

18 Claims, 5 Drawing Sheets

OTHER PUBLICATIONS

Tindle, et al., "Virology", *Chimeric Hepatisi B Core Antigen Particles Containing B– and Th–Epitopes of Human Papillomavirus type 16 E7 Protein Induce Spec. Antibody and T–Helper*... pp. 547–557 (1994).

Kirnbauer et al., "Proc. Natl. Acad. Science", Papillomavirus L1 major capsid protein self–assembles into *virus–like particles that are highly immunogenic*, vol. 89, pp. 12180–12184 (1992).

Carter et al., "Virology", *Expression of Human Papillomavirus Proteins in Yeast Saccharomyces Cerevisiae*, pp. 513–521 (1991).

Strike et al., Expression in *Escherichia coli* of Seven DNA Fragments Comprising the Complete L1 and L2 Open Reading Frames of Human Papillomavirus Type 6b and Localication of the 'Common Antigen' Region, Virology, pp. 543–555 (1989).

Schafer et al., *Immune Response to Human Papillomavirus 16 L1E7 Chimeric Virus–Like Particles: Induction of Cytotoxic T Cells and Specific Tumor Protection*, "Int. J. Cancer" vol. 81, pp. 881–888 (1999).

Rose et al., *Expression of the full–length products of the human papillomavirus type 6b (HPB–6b) and HPV–11 L2 open reading frames by recombinant baculovirus, and antigenic comparisons with HPV–11 whole virus particles.* "Journal of General Virology", vol. 71, pp. 2725–2729 (1990).

Muller et al., *Chimeric papillomavirus–like Particles*, "Virology", pp. 93–111 (1997).

J. Zhou et al., "Virology", vol. 185, *Identification of the Nuclear Localization Signal of Human Papillomavirus Type 16 L1 Protein*, pp. 625–632, (1991).

R. Kirnbauer et al., "Journal of Virology", vol. 67 No. 12, *Efficient Self–Assembly of Human Papillomavirus Type 16 L1 and L1–L2 into Virus–Like Particles*, pp. 6929–6936, (Dec. 1993).

J.A. Rawls et al., "Journal of Virology", vol. 64 No. 12, *Chemical Synthesis of Human Papillomavirus Type 16 E7 Oncoprotein: Autonomous Protein Domains for Induction of Cellular DNA Synthesis and for trans Activation*, pp. 6121–6129, (Dec. 1990).

Paintsil, et al., "Virology", vol. 223, pp. 238–244, (1996).

Greenstone et al., "Proc. Natl. Acad. Sci. USA" *Chimeric Papillomavirus Virus–Like Particles Elicit Antitumor Immunity Against The E7 Oncoprotein in an HPV16 Tumor Model*, vol. 95, pp. 1800–1805, (Feb. 1998).

Zhou et al., "Abstract From the 13th International Papillomavirus Conference", *Determination of L1 Sequences Required for 1Assembly of Bovine Papillomavirus (BPV) Capsids*, Amsterdam, Netherlands, (Oct. 1994).

Zhou et al., "Glycosylation of Human Papillomavirus Type 16 L1 Protein", *Virology*, 194, pp. 210–218, (1993).

M. Li, et al., *Expression of the Human Papillomarvirus Type 11 L1 Capsid Protein in Escherichia coli: Characterization of Protein Domains Involved in DNA Binding and Capsid Assembly*, Journal of Virology, vol. 71, No. 4, pgs. 2988–2995, (1997).

Altmann et al. "Towards HPV Vaccination," in *Viruses and Cancer*, Eds. Minson et al., Cambridge University Press, 71–80 (1994).

Balsley et al. "Progress in the Development of Human Papillomavirus Vaccines for HPV–11 and HPV–16/18 and Mapping of a Critical Neutralizing Epitope" Abstract from HPV 2000 Int. Papillomavirus Conf. 366.

Breitburd et al. J. Virol., 69: 3959–3963 (1995).

Campo "Vaccination Against Papillomavirus in Cattle" in *Current Top Microbiol. Immunol: Human Pathogenic Papillomarivuses*, Ed. Zur Hausen, Springer Verlag, Berlin, 186:255–266.

Christensen et al. "Human Papillomavirus Types 6 and 11 Have Antigenically Distinct Strongly Immunogenic Conformationally Dependent Neutralizing Epitopes," *Virology*, 205:329–335 (1994).

Christensen et al. "Assembled Baculovirus–Expressed Human Papillomavirus Type 11 L1 Capsid Protein Virus–Like Particles Are Recognized by Neutralizing Monoclonal Antibodies and Induce High Titres of Neutralizing Antibodies," *J. Gen. Virol.*, 75:2271–2276 (1994).

Crum et al. "Coexpression of the Human Papillomvirus Type 16 E4 and L1 Open Reading Frames in Early Cervical Neoplasia" *Virology*, Academic Press, 178: 238–246 (1990).

Crum et al. "Human Papillomavirus Type 16 and Early Cervical Neoplasia" *N. Engl. J. Med.*, Boston, MA, 310:880–883 (1984).

Dillner et al. "Antibodies Against Linear and Conformational Epitopes of Human Papillomavirus Type 16 that Independently Associate with Incident Cervical Cancer," *Int. J. Cancer*, 60: 377–382 (1995).

Doorbar et al. "Identification of the Human Papilloma Virus–1a E4 Gene Products" *EMBO J.*, 5: 355–362 (1986).

Fife et al. "A Dose–Ranging Study of the Safety and Immunogenicity Profiles of an HPV 11L1 VLP Candidate Vaccine in Young Healthy Woman" Abstract from HPV 2000 Int. Papillomavirus Conf. 364.

Ghim et al. "HPV–1 L1 Protein Expressed In cos Cells Displays Comformational Epitopes Found on Intact Virions", *Virology* 190: 548–552.

Gissmann "Human Papillomaviruses and Genital Cancer Seminars" in Cancer Biology, 3:253–261 (1992).

Greenfield et al. "Human Papillomavirus 16 E7 Protein is Associated with the Nuclear Matrix" *Proc. Natl. Acad. Sci. USA*, 88: 11217–11221 (1991).

Hagensee et al. "Three–Dimensional Structure of Vaccinia Virus–Produced Human Papillomavirus Type 1 Capsids," *J. Virol.*, 68: 4503–4505 (1994).

Harry et al. "A Safety and Immonogenicity Trial of a Human Papillomavirus Type 16 L1 Virus–Like Particle Vaccine in Healthy Young Adult Human Volunteers" Abstract from HPV 2000 Int. Papillomavirus Conf. 362.

Heim et al. "Serum IgG, IgM and IgA Reactivity to Human Papillomavirus Types 11 and 6 Virus–Like Particles in Different Gynecologic Patient Groups," *J. Infect. Dis.*, 172: 395–402 (1995).

Hofmann et al. "Sequence Determination of Human Papillomavirus Type 6a and Assembly of Virus–Like Particles in *Saccharomyces cerevisiae,*" *Virology*, 209: 506–518 (1995).

Ikenberg "Human Papillomavirus DNA in Invasive Genital Carcinomas" in *Genital Papillomavirus Infections*, Eds. Gross et al., 87–112 (1990).

Jochmus et al. "Chimeric Virus–Like Particles of the Human Papillomavirus Type 16 (HPV 16) as a Prophylactic and Therapeutic Vaccine", *Archives of Medical Research*, 30: 269–274 (1999).

Jochmus–Kudielka et al. "Antibodies Against the Human Papillomavirus Type 16 Early Proteins in Human Sera: Correlation of Anti–E7 Reactivity with Cervical Cancer" J. Natl. Cancer Inst., 81: 1698–1704 (1989).

Kaufmann et al. "HPV16 L1E7 Chimeric Virus–Like Paticles Induce Specific HLA–Restricted T Cells in Human After In Vitro Vaccination", *Int. J. Cancer*, 92: 285–293 (2001).

Kirnbauer et al. "A Virus–Like Particle Enzyme–Linked Immunsorbent Assay Detects Serum Antibodies in a Majority of Women Infected With Human Papillomavirus Type 16," *J. Natl. Cancer Inst.*, 86: 494–499 (1994).

Lecann et al. "Detection of Antibodies against Human Papillomavirus (HPV) Type 16 Virions by Enzyme–Linked Immunosorbent Assay Using Recombinant HPV 16 L1 Capsids Produced by Recombinant Baculovirus," *J. Clin. Microbiol.*, 33: 1380–1382 (1995).

Lecann et al. "Self–Assembly of Human Papillomavirus Type 16 Capsids by Expression of the L1 Protein in Insect Cells," FEMS Microb. Lett., 117: 269–274 (1994).

Liu et al. "Mucosal Immunization with Papillomavirus Virus–Like Particles Ellicits Systemic and Mucosal Immunity in Mice," *Virology*, 252: 39–45 (1998).

Lowy et al. "Genital Human Papillomavirus Infection," *Proc. Nat. Acad. Sci. USA*, 91: 2436–2440 (1994).

Müller et al. "Papillomavirus Capsid Binding and Uptake by Cells from Different Tissues and Species," *J. Virol*, 69: 948–954 (1995).

Nasseri et al. "Genetic Analysis of CRPV Pathogenesis: the L1 Open Reading Frame is Dispensable for Cellular Transformation But Is Required for Papilloma Formation", *Virology*, Academic Press, 170:321–325 (1989).

Nonnenmacher et al. "Serologic Response to Human Papillomavirus Type 16 (HPV–16) Virus–Like Particles in HPV–16 DNA–Positive Invasive Cervical Cancer and Cervical Intraepithelial Neoplasia Grade III Patients and Controls from Columbia and Spain," *J. Infect. Dis.*, 172:19–24 (1995).

Parkin et al. "Estimates of the Worldwide Frequency of Sixteen Major Cancers in 1980", *Int. J. Cancer*, Alan R. Liss, Inc., 41: 184–197 (1988).

Poland et al. "A Randomized, Double–Blind, Placebo–Controlled Trial of the Immunogenicity and Reactogenicity of a Novel HPV 16 Vaccine: Preliminary Results" Abstract from HPV 2000 Int. Papillomavirus Conf. 363.

Pushko et al. "Sequence Variation in the Capsid Protein Genes of Human Papillomavirus Type 16" *J. Gen. Virol.*, 75:911–916 (1994).

Roden et al. "Papillomavirus L1 Capsids Agglutinate Mouse Erythrocytes through a Proteinaceous Receptor," *J. Virol.*, 69:5147–5151 (1995).

Roden et al. "In Vitro Generation and Type–Specific Neutralization of a Human Papillomavirus Type 16 Virion Pseudotype", *J. Virol.*, 70:5875–5883 (1996).

Roden et al. "Interaction of Papillomavirus with the Cell Surface," *J. Virol.*, 68:7260–7266 (1994).

Rose et al. "Serological Differentiation of Human Papillomavirus Types 11, 16 and 18 Using Recombinant Virus–Like Particles," *J. Gen. Virol.*, 75: 2445–2449 (1994).

Rose et al. "Human Papillomavirus (HPV) Type 11 Recombinant Virus–Like Particles Induce the Formation of Neutralizing Antibodies and Detect HPV–Specific Antibodies in Human Sera," *J. Gen. Virol.*, 75:2075–2079 (1994).

Rudolf et al. "Induction of HPV16 Capsid Protein–Specific Human T Cell Responses by Virus–Like Particles", *Biol. Chem.*, 380: 335–340 (1999).

Sapp et al. "Analysis of Type–Restricted and Cross–Reactive Epitopes on Virus–Like Paticles of Human Papillomavirus Type 33 and Infected Tissues Using Monoclonal Antibodies to the Major Capsid Protein" J. Gen. Virology, 75: 3375–3383 (1994).

Sasagawa et al. "Synthesis and Assembly of Virus–Like Particles of Human Papillomavirus Type 6 and Type 16 Fission Yeast *Schizosaccharomyces pombe,*" *Virology*, 206: 126–135 (1995).

Tindle et al. "Immune Response to Human Papillomavirus and the Prospects for Human Papillomavirus–Specific Immunization" in *Current Topics in Microbiol. Immunol: Human Pathogenic Papillomaviruses*, Ed. zur Heusen, Springer Verlag, Berlin, 186:217–254 (1994).

Toes et al. "An Adenovirus Type 5 Region 1B–Encoded CTL Epitope–Mediating Tumor Eradication by CTL Clones Is Down–Modulated by an Activated ras Oncogene", *The Journal of Immunology*, 154: 3396–3405 (1995).

Toes et al. "Peptide Vaccination Can Lead to Enhanced Tumor Growth Through Specific T–cell Tolerance Induction", *Proc. Natl. Acad. Sci.*, 93: 7855–7860 (1996).

Volpers et al. "Binding and Internalization of Human Papillomavirus Type 33 Virus–Like Particles by Eukaryotic Cells," *J. Virol.*, 69: 3258–3264 (1995).

Volpers et al. "Assembly of the Major and the Minor Capsid Protein of Human Papillomavirus Type 33 into Virus–like and Tubular Structures in Insect Cells," *Virology*, Academic Press, 200: 504–512 (1994).

von Knebel Doeberitz et al. "Correlation of Modified Human Papillomavirus Early Gene Expression with Altered Growth Properties in C4–1 Cervical Carcinoma Cells" *Cancer Res.*, 48: 3780–3786 (1988).

Wettstein "State of Viral DNA and Gene Expression in Benign vs. Malignant Tumors" in Papillomaviruses and Human Cancer, Eds. H. Pfister, CRC Press, Boca Raton, Florida, USA, 155–179 (1990).

Wikstrom et al. "Identification of Human Papillomavirus Seroconversions," *J. Gen. Virol.*, 76: 529–539 (1995).

Zhou et al. "Synthesis and Assembly of Infectious Bovine Papillomavirus Particles in Vitro" *J. Gen. Virol.*, Great Britain, 74 763–768 (1993).

Zhou et al. "Glycosylation of Human Papillomaviru Type 16 L1 Protein" *Virology*, 194: 210–218 (1993).

Zur Hausen "Papillomaviruses as Carcinomaviruses" in *Advances in Viral Oncology*, Ed., Klein et al., Raven Press, New York 8:1–26 (1989).

\* cited by examiner

DAYS AFTER TUMOUR INOCULATION

TABLE 1

TUMOUR PROTECTION AFTER IMMUNIZATION WITH L1ΔCE7$_{1-60}$ CVLPs

| VACCINE | NUMBER OF MICE | NUMBER OF TUMOURS |
|---|---|---|
| HS BUFFER | 18 | 16 |
| L1ΔC VLPs | 13 | 11 |
| L1ΔCE7$_{1-55}$ CVLPs | 10 | 7 |
| L1ΔCE7$_{1-60}$ CVLPs | 13 | 1 |

MEDICAMENT FOR THE AVOIDANCE OR TREATMENT OF PAPILLOMAVIRUS-SPECIFIC TUMOUR

This application is a continuation of PCT/EP99/01996, filed Mar. 24, 1999, which claims the benefit of priority of a German application No. 198 12 941.6, filed Mar. 24, 1998, the contents of each being expressly incorporated herein by reference.

The present invention relates to a medicament for the avoidance or treatment of human papillomaviruses (HPV)-specific tumour comprising at least one fusion protein from at least one L1 protein of one or more papillomaviruses and at least one E protein of one or more papillomaviruses and, if appropriate, suitable additives and/or excipients, the fusion protein containing no papillomavirus-unspecific epitopes.

Papillomaviruses, also called wart viruses, are double-stranded DNA viruses having a genome size of approximately 8000 base pairs and an icosahedral-like capsid having a diameter of about 55 nm. To date, more than 100 different human papillomavirus types are known, of which some, e.g. HPV-16, HPV-18, HPV-31, HPV-33, HPV-39, HPV-45, HPV-52 or HPV-58, can cause malignant tumours and others, e.g. HPV-6, HPV-11 or HPV-42, can cause benign tumours.

Electron-microscopic analysis of BPV-1 and HPV-1 shows that the viruses are constructed from 72 pentameric capsomers, which in turn consist of five L1 molecules (Baker, T. et al. (1991) Biophys. J., 60, 1445).

The genome of the papillomaviruses can be subdivided into three areas: the first area concerns a non-coding region which contains regulation elements for the transcription and replication of the virus. The second region, the so-called E (early) region, contains various protein-coding sections E1–E7, of which, for example, the E6 protein and the E7 protein is responsible for the transformation of epithelial cells and the E1 protein controls the DNA copy number. The E6 region and E7 region are so-called oncogenes, which are also expressed in malignantly degenerate cells. The third region, also called the L (late) region, contains two protein-coding sections L1 and L2, which code for structural components of the virus capsid. The L1 protein is present to over 90% in the viral capsid, the ratio of L1:L2 in general being 30:1.

HPV-6 and HPV-11 have been held responsible, inter alia, for genital warts; some papillomavirus types such as HPV-16, HPV-18, HPV-31, HPV-33, HPV-39, HPV-45, HPV-52 and HPV-58 are associated with malignant tumours of the ano-genital tract. In over 50% of the cases, HPV-16 is connected with cervical cancer (carcinoma of the cervix). HPV-16 is therefore the main risk factor for the formation of cervical neoplasias. In addition, the immune system plays an important role in the progress of the disease. Thus cellular immune responses and in particular antigen-specific T lymphocytes are supposedly important for the defence mechanism. It has furthermore been found that in high-grade cervical intraepithelial neoplasias (CIN II/III) and cervical tumour the E7 gene is expressed constitutively in all layers of the infected epithelium. The E7 protein is therefore considered as a potential tumour antigen and as a target molecule for activated T cells (see, for example, WO 93/20844). The E7-induced cellular immune response in the patient, however, is apparently not strong enough to influence the course of the disease. The immune response can possibly be amplified by suitable vaccines.

It has now been possible to show that the expression of the L1 gene or the coexpression of the L1 and L2 gene forms virus-like particles (VLPs). It was possible to use the VLPs for the formation of neutralizing antibodies in various animal systems. The formation of virus-neutralizing antibodies, however, is of relatively low clinical importance if the virus infection has already taken place, since for the elimination of virus-infected cells a virus-specific cytotoxic T-cell (CTL) response appears to be necessary. So-called chimeric papillomavirus-like particles (CVLPs) were therefore developed which consist of a chimeric L1–E7 protein (Müller, M. et al. (1997) Virology, 234, 93): some CVLPs induce an E7-specific CTL response in mice, although experiments failed to induce antibodies by immunization of mice with CVLPs against E7 (Müller, M. et al. (1997), supra). In addition, neutralizing antibodies of HPV-associated disorders in patients appear to limit the immune response to administered L1 protein (Müller, M. et al. (1997), supra). CVLPs, however, are still of interest for the development of a vaccine, as the E7 proteins of tumour cells presented via MHC molecules of class I would represent target molecules of CTLs.

Peng et al. (1998) Virology, 240, 147 now describe CVLPs consisting of C-terminally truncated L1 of the bovine papillomavirus (BPV) and HPV-16E7$_{49-57}$, which induce E7-specific cytotoxic T cells after inoculation of C57B1/6 mice and protect against the growth of E7-expressing tumours. Greenstone et al. (1998) Proc. Natl. Acad. Sci. USA, 95, 1800 describe CVLPs consisting of HPV-16L1 plus HPV-16L2 fused to the full-length HPV-16E7 protein, which protect against the growth of epithelial E7-expressing tumour cells after immunization of C57B1/6 mice, cytotoxic T cells, however, not being detected and thus the induction of the immune response appearing to be less efficient.

VLPs and CVLPs are in general prepared by means of genetic engineering by expression of the corresponding genes coding for one or more L proteins or L and E proteins in suitable expression systems. The corresponding genes are described, for example, in Kirnbaum, R. et al. (1994) J. Virol., 67, 6929–6936 or obtainable via the EMBL databank. The accession numbers are, for example, for HPV18: PAPHPV18; for HPV31: PAPPPH31; for HPV33: PAPPPH33 or for HPV58: PAPPPH58.

Suitable expression systems are, for example, yeasts modified by genetic engineering, e.g. *Saccharomyces* (*cerevisiae*), *Pichia* (*pastoris*), *Kluyvermyces* (*lactis*), *Schizosaccharomyces* (*pombe*) or *Hansenula* (*polymorpha*) (Carter, J. J. et al. (1991), Virology, 182, 513), insect cells, such as, for example, *Trichoplusia ni* High Five (see, for example, Müller et al. (1997), supra) or prokaryotic cells (see, for example, WO 96/11272). In the case of the production of the particles in prokaryotic cells, these are in general deposited in the cell and form so-called inclusion bodies, which then have to be renatured and brought into solution. For use of the particles or capsids produced by genetic engineering or their precursors, the so-called capsomers, further purification steps are necessary after expression.

A crucial disadvantage of the active compounds against HPV described in the literature is, however, that on the one hand they exhibit only a slight action and on the other hand that it has not been possible to date to show any effective immunotherapy of papillomavirus-specific tumour.

It was therefore the object of the present invention to make available a medicament with which human papillomavirus-specific tumour can be avoided or treated effectively, which can be produced simply and which appears to be suitable for licensing as a medicament.

It has now surprisingly been found that the medicament according to the invention is effective against HPV-specific tumour.

One subject of the present invention is therefore a medicament for the avoidance or treatment of human papillomavirus (HPV)-specific tumour comprising at least one fusion protein from at least one L1 protein of one or more papillomaviruses and at least one E protein of one or more papillomaviruses and, if appropriate, suitable additives and/or excipients, the fusion protein comprising no papillomavirus-unspecific epitopes.

Papillomavirus-unspecific epitopes within the meaning of the present invention are understood in general as meaning epitopes in the fusion protein which are caused by a foreign protein fraction, by post-translational modifications or by misfolding of papillomavirus-specific proteins.

The papillomavirus-unspecific epitopes are, for example, a reason for the fact that although neutralizing antibodies or CTL immune responses are induced, the papillomavirus-specific tumour cannot be effectively avoided or controlled, as the immunological action is weakened by unspecific antibodies or CTLs or immunological side effects interfere with the action of the actual active compound.

The medicament according to the invention is preferably effective for the avoidance or treatment of benign or malignant tumour, in particular of carcinoma of the larynx, cervix, penis, vulva or anus, including their preliminary stages, such as, for example, high-grade CIN (cervical intraepithelia neoplasia).

In a further preferred embodiment, the medicament according to the invention contains no adjuvant, i.e. no substance which amplifies the immunity of the papillomavirus-specific protein, as the presence of an L protein in particular, especially of L1, already adequately amplifies the immunity. This property is particularly advantageous in the licensing as a medicament or diagnostic, as the only immuno-stimulating materials licensed by the licensing authorities at present are aluminium salts. Moreover, undesired side effects are avoided by the omission of adjuvants and/or other excipients and additives.

As already mentioned above, a further significant problem in the use of capsids and capsomers as medicaments is their poor solubility. Thus capsids or capsomers of HPV-16, for example, tend to aggregate, whereby the solubility is significantly reduced. The solubility of the capsids or capsomers, which in some cases is low, leads not only to a loss of yield, but also to complicated use as a medicament.

In a further preferred embodiment, the medicament according to the invention therefore contains as a suitable additive or excipient about 0.3 to about 4 M, preferably about 0.4 to about 3 M, in particular about 0.5 to 2 M, especially about 1 to about 2 M, of a salt having a pH of about 7.3 to about 7.45, preferably about 7.4.

The advantage of this salt solution is that the fusion protein remains in solution or is present finely divided as a suspension, i.e., in general more than about 90%, especially more than about 95%, of the fusion protein remains in solution and also does not deposit for a period of time of at least about 12 hours. The fusion protein is also not significantly sedimentable by centrifugation at a maximum of 5000 g.

The salt is in general an alkali metal or alkaline earth metal salt, preferably a halide or phosphate, in particular an alkali metal halide, especially NaCl and/or KCl. Use of NaCl is particularly preferred for the production of a pharmaceutical formulation.

The pH of the medicament is in general adjusted using a suitable organic or inorganic buffer, such as, for example, preferably using a phosphate buffer, tris buffer (tris (hydroxymethyl)aminomethane), HEPES buffer ([4-(2-hydroxyethyl)piperazino]ethanesulphonic acid) or MOPS buffer (3-morpholino-1-propanesulphonic acid). The choice of the respective buffer in general depends on the desired buffer molarity. Phosphate buffer is suitable, for example, for injection and infusion solutions.

Suitable further additives and/or excipients which serve, for example, for the further stabilization of the papillomavirus-specific protein in the medicament according to the invention are, for example, detergents, such as, for example, Triton X-100 or sodium deoxycholate, but also polyols, such as, for example, polyethylene glycol or glycerol, sugars, such as, for example, sucrose or glucose, zwitterionic compounds, such as, for example, amino acids such as glycine or in particular taurine or betaine and/or a protein, such as, for example, bovine or human serum albumin. Detergents, polyols and/or zwitterionic compounds are preferred. Other additives and/or excipients are protease inhibitors, such as, for example, aprotinin, ε-aminocaproic acid or pepstatin A. Those additives are preferred which induce no immunological side effects.

The terms L1/L2 protein and E protein are understood within the meaning of the present invention as meaning both the full-length proteins and their mutants, such as, for example, deletion mutants.

In a further preferred embodiment, the fusion protein according to the invention contains a deleted L protein, preferably a deleted L1 and, if appropriate, L2 protein. The deletion has the advantage that particularly active different proteins, for example papillomavirus-specific E protein sequences, can be inserted into the deleted area, whereby the application area of the composition according to the invention can be widened. An L protein having a C terminal deletion and in particular a C-terminally deleted L1 protein is particularly preferred. The C-terminal deletion has the advantage that the efficiency of the formation of virus-like particles can be increased, since the nuclear location signal located at the C terminus is deleted. The C-terminal deletion is therefore preferably up to about 35 amino acids, in particular about 25 to about 35 amino acids, especially about 32 to 34 amino acids. For example, a C-terminal deletion of the HPV-16L1 protein 32 amino acids long is adequate to be able to increase the formation of virus-like particles by at least about 10-fold.

In a further preferred embodiment, the E protein is also deleted, especially the E6 and/or E7 protein. It is particularly preferred if the C-terminal part of the E protein is deleted, preferably the C-terminal part of the E7 protein, as these constructs can preferably form capsomers and/or capsids in combination with deleted L protein. Deletions of up to 55 amino acids are particularly preferred, preferably about 5 to about 55 amino acids, in particular about 32 to about 43 amino acids.

A particularly preferred construct is, for example, E7 having the N-terminal amino acids 1 to about 60, as this construct contains a mouse epitope for the activation of cytotoxic T lymphocytes, which is located in the area of the amino acids 49–57. Another preferred construct is E7 having the N-terminal amino acids 1 to about 55, which preferably forms capsomers and capsids in combination with deleted L protein, as this construct does not contain E7-specific sequences in the area of the amino acids 56–70, which can interfere with the formation of capsids. An L1 protein of HPV-16 C-terminally deleted by 32 amino acids and which is linked to an E7 protein of HPV-16 having the amino acids 1–55 or 1–60 is particularly preferred. These constructs not only induce neutralizing antibodies or a specific CTL response, but on the one hand prevents the formation of tumours and on the other hand cause regression of already existing tumours in animal experiments. E7 having the amino acids 1–60 especially exhibits a marked prophylactic and therapeutic action in tumours. A particularly preferred embodiment of the present invention is therefore an L1ΔE7$_{1-x}$ fusion protein, preferably in the form of a CVLP$_s$, in particular of HPV16, x being an integer from 55 up to and including 60, and in particular an L1ΔE7$_{1-55}$ or L1ΔE7$_{1-60}$ fusion protein.

The present invention therefore also relates to the use of the constructs according to the invention for the production of a medicament, on the one hand for the connection of HPV-specific tumours and on the other hand for the regression of already existing HPV-specific tumours.

For the production of a medicament which is active both prophylactically and therapeutically, it is preferred if the described papillomavirus-specific fusion protein is present in the form of a capsid and/or capsomer, since the immune reaction can additionally be markedly increased by the capsids and/or capsomers and in particular by the fraction of L protein. Preferred fusion proteins which are suitable for capsid and/or capsomer formation are therefore, for example, fusion proteins from deleted L1 and E7, E6 and/or E1.

Capsids within the meaning of the present invention are viral or virus-like structures in a generally icosahedral form, which in general are constructed of 72 capsomers.

Capsomers within the meaning of the present invention are assembled proteins comprising at least one papillomavirus structural protein, preferably L1 or deletions of L1. For example, 5 fusion proteins according to the invention can be assembled to give a capsomer which in turn can be assembled to give a capsid.

For the production of a human medicament, proteins or peptides of the human papillomavirus (HPV) and preferably of HPV-6, HPV-11, HPV-16, HPV-18, HPV-31, HPV-33, HPV-35, HPV-39, HPV-45, HPV-52 and/or HPV-58, in particular HPV-16, HPV-18, HPV-31 and/or HPV45 are suitable for the constructs described. Especially for the production of a combination vaccine, it is advantageous to combine proteins or peptides from various HPV types, for example a combination of HPV-16 and HPV-18 or HPV-18, HPV-31, HPV-45 and HPV-58 in the case of, for example, carcinoma of the cervix or HPV-6 and HPV-11 in the case of, for example, condylomas.

A further subject of the present invention is a process for the production of a medicament according to the invention, in which a suitable cell comprising a suitable expression vector which codes for the fusion protein mentioned is cultured under suitable conditions, the expression product is isolated and, if appropriate, suitable additives and/or excipients are added.

The expression vectors can be, for example, prokaryotic or eukaryotic expression vectors. Examples of prokaryotic expression vectors are, for expression in *E. coli*, e.g. the vectors pGEM or pUC derivatives (see, for example, WO 96/11272). Examples of eukaryotic expression vectors are, for expression in *Saccharomyces cerevisiae*, e.g. the vectors p426Met25 or p426GAL1 (Mumberg et al. (1994) Nucl. Acids Res., 22, 5767–5768, Carter, J. J. et al. (1991) supra) and, for expression in insect cells, e.g. Baculovirus vectors, in particular the *Autographa Californica* virus, such as disclosed in EP-B1-0 127 839 or EP-B1-0 549 721 (see, for example, also WO 94/20137), and, for expression in mammalian cells, e.g. the vectors Rc/CMV and Rc/RSV or SV40 vectors which are all generally obtainable. However, commercially obtainable Baculovirus expression systems are also suitable, such as, for example, the Baculo Gold™ transfection kit from Pharmingen or the Bac-to-Bac™ Baculovirus expression system from Gibco BRL. Further suitable expression systems are recombinant vaccinia viruses (see, for example WO 93/02184).

In general, the expression vectors also contain promoters suitable for the respective host cell, such as, for example, the trp promoter for expression in *E. coli* (see, for example, EP-B1-0 154 133), the ADH2 promoter for expression in yeasts (Russel et al. (1983), J. Biol. Chem. 258, 2674–2682), the Baculovirus polyhedrin promoter for expression in insect cells (see, for example EP-B1-0 127 839 or U.S. Pat. No. 5,004,687) or the early SV40 promoter or LTR promoters, e.g. of MMTV (mouse mammary tumour virus; Lee et al. (1981) Nature 214, 228–232).

Suitable host cells are, for example, the *E. coli* strains DH5, HB101 or BL21, the yeast strains Saccharomyces, Pichia, Kluyvermyces, Schizosaccharomyces or Hansenula (Carter, J. J. et al. (1991), Virology, 182, 513), the insect cell line Lepidopteran, e.g. from *Spodoptera frugiperda, Trichoplusia ni, Rachiplusia ou* or *Galleria Mellonela* or the animal cells COS, C127, Vero, 293 and HeLa, which are all generally obtainable (see, for example, WO 94/00152).

The coding nucleic acids for the individual papillomavirus-specific proteins can be isolated and cloned, for example, from a gene bank by means of a PCR (polymerase chain reaction) amplification. For example, the genome of BPV-1 is generally obtainable under the GenBank Accession No. X02346 or HPV-16 under the GenBank Accession No. K02718. An HPV-16 L1 sequence is also disclosed, for example, in WO 94/05792. The sequence of the 98 amino acid-long HPV16 E7 protein is described, for example, in Seedorf et al. (1985) Virology, 145, 181–185. Another method of obtaining the desired nucleic acids is to isolate the papillomavirus-specific genes directly from warts or tumours by means of PCR. Suitable primers for the E6 and E7 genes from HPV-16 and BPV-18 are disclosed, for example, in WO 93/21958. Further references for the desired nucleic acids are, for example, Kirnbaum, R. et al. (1994), supra or the clones deposited in the EMBL databank already mentioned above.

In a further preferred embodiment, the expression vector is constructed such that the expressed fusion protein is extended by no further amino acids caused by the vector. This is achieved, for example, by removing undesired nucleotides which code for additional amino acids by mutagenesis in a PCR reaction by means of suitable primer oligonucleotides (Ho et al. (1989) Gene, 77, 51–59). In this way, a fusion protein is obtained which is free of additional amino acids and thus free of possible additional foreign epitopes which can cause immunological side reactions.

After the expression of the described fusion protein, it is preferred to purify this further or to renature it. Examples of chromatographic purification processes are found in Hjorth, R. & Moreno-Lopez, L. (1982) J. Virol. Meth. 5, 151; Nakai, Y. et al. (1987) J. Gen. Virol., 68, 1891; Hofmann, K. J. et al. (1995) Virology, 209, 506; Rose, R. C. et al. (1993) J. Virol., 67, 1936, Sasagawa, T. et al. (1995) Virology, 206, 126 or WO 95/31532.

In general, the medicament can be administered orally, parenterally, such as, for example, subcutaneously, intramuscularly or via the mucous membrane, in liquid or suspended form, in the form of an elixir or as capsules, preferably as an injection or infusion solution. In the case of the formulations according to the invention, an adjuvant can be dispensed with, which is particularly advantageous.

A further subject of the present invention therefore relates to the use of the formulation according to the invention as an injection or infusion solution.

Injection solutions are in general used if only relatively small amounts of a solution or suspension, for example about 1 to about 20 ml, are to be administered to the body. Infusion solutions are in general used if a larger amount of a solution or suspension, for example one or more liters, are to be administered. Since, in contrast to the infusion solution, only a few milliliters are administered in the case of injection solutions, small differences from the pH and from the osmotic pressure of the blood or the tissue fluid in the injection do not make themselves noticeable or only make themselves noticeable to an insignificant extent with respect to pain sensation. Dilution of the formulation according to the invention before use is therefore in general not necessary. In the case of the administration of relatively large amounts, however, the formulation according to the invention should be diluted briefly before administration to such an extent that an at least approximately isotonic solution is obtained. An example of an isotonic solution is a 0.9% strength sodium chloride solution. In the case of infusion, the dilution can be carried out, for example, using sterile water while the administration can be carried out, for example, via a so-called bypass.

The figures and the following examples are intended to illustrate the invention in greater detail without restricting it.

EXAMPLES

1. Preparation of Chimeric Genes Coding for HPV16L1E7 Fusion Proteins

The HPV-16L1 open reading frame (ORF) was excized from the plasmid HPV-16-114/k-L1/L2-pSynxtVI$^-$ (Kirnbauer, R. et al. (1994) J. Virol. 67, 6929) using the restriction endonuclease BgIII and cloned into the BamHI site in the vector pUC19 (New England Biolabs).

For the preparation of HPV-16L1ΔC, two primers were constructed which are complementary to HPV-16L1 ORF. The first primer has the sequence
AAAGATATCTTGTAG-
TAAAAATTTGCGTCCTAAAGGAAAC (SEQ ID NO:1) and the second primer
AAAGATATCTAATCTACCTCTACAACT-
GCTAAACGCAAAAAACG. (SEQ ID NO:2)

Both primers encode an EcoRV restriction enzyme cleavage site 5'. In the primers lying downstream, a TAA translation stop codon follows the EcoRV site in order to delete the last 34 amino acids of the HPV16L1 ORF. The PCR reaction was carried out in order to amplify the entire L1 ORF and the entire vector. The linear product was cleaved with EcoRV and circularized with T4 DNA ligase and *E. coli* DH5α cells were transformed. The clones were analysed for the presence of an EcoRV site. The construct pUCHPV16L1ΔC obtained was used in order to clone the ORF of HPV16E7 1–50 into the EcoRV site.

For the cloning of the fragment, primers having a 5'EcoRV restriction enzyme cleavage site were used. The following primer pair was used:
AAAAGATATCATGCATGGAGATACACCTACATTGC (SEQ ID NO:3)
and
TTTTGATATCGGCTCTGTCCGGTTCTGCTTGTCC. (SEQ ID NO:4)

The PCR products were cleaved with EcoRV and inserted into the EcoRV site of the modified L1 gene.

For the elimination of the EcoRV sites, two PCR reactions were carried out in order to amplify two overlapping fragments of the clone pUC-HPV16L1ΔCE7 1–50. The resulting DNA fragments overlapped in the position of the L1/E7 boundary (Four Primer PCR, Ho, S. N. et al (1989) Gene 77, 51). However, the primers did not contain the two EcoRV restriction enzyme cleavage sites. Fragment 1 was prepared using the primers P1 and P2 and fragment 2 using the primers P3 and P4.
P1: GTTATGACATACATACATTCTATG (L1) (SEQ ID NO:5)
P2: CCATGCATTCCTGCTTGTAGTAAAAAT-FTGCGTCC (E7) (SEQ ID NO:6)
P3: CTACAAGCAGGAATGCATGGAGATACACC(E7) (SEQ ID NO:7)
P4: CATCTGAAGCTTAGTAATGGGCTCTGTC-CGGTTCTG (E7) (SEQ ID NO:8)

A tenth of the purified products was mixed and used as a matrix in the PCR reaction with the primers P1 and P4 exclusively. The resulting product was cleaved using EcoNI (L1) and HindIII (downstream of the stop codon on the primer P4) and used in order to replace an EcoNI/HindIII fragment of the cloned HPV16L1 ORF. The resulting clone therefore differs from the clone HPV16L1ΔCE7 1–50 by the loss of the two internal EcoRV restriction enzyme cleavage sites and the corresponding non-HPV amino acids Asp and Ile between the L1 ORF and E7 and downstream of E7. The first EcoRV site was replaced by the original L1 amino acids in this position (AlaGly). The second EcoRV site was replaced by a translation stop signal. This clone (BPV16L1ΔC*E7 1–52) additionally contains the first 52 amino acids of HPV16E7. Clone HPV16L1ΔC*E7 1–52 was used for the preparation of the clones HPV16L1ΔC*E7 1–55, 1–60 and 1–65 with the aid of the primer P1 in combination with P5, P6 and P7.

P5: CATCTGAAGCTTATCAATAUG-TAATGGGCTCTGTCCG (E7 1–55) (SEQ ID NO:9)
P6: CATCTGAAGCTTACTTGCAACAAAAGGT-TACAATATTGTAATGGGCTCTGTCCG (E7 1–60) (SEQ ID NO:10)
P7: CATCTGAAGCTTAAAGCGTAGAGTCA-CACTTGCAACAAAAGGTTACAATATTG-TAATGGGCTCTGTCCG (E7 1–65). (SEQ ID NO:11)
HPV16L1ΔC*E7 1–70 was prepared using the clone HPV16L1ΔC*E7 1–65 and the primers P1 and P8.
P8: CATCTGAAGCTTATTGTACGCACAAC-CGAAGCGTAGAGTCACACTTG (SEQ ID NO:12)

In all cases, EcoNI and HindIII were used in order to replace the corresponding fragments. The clones were analysed by DNA sequencing.

2. Preparation of Recombinant Baculoviruses

*Spodoptera frugiperda* (Sf9) cells were used as a monolayer or in suspension culture in TNM-FH insect medium (Sigma, Deisenhofen) with 10% foetal calf serum and 2 mM glutamine. Recombinant baculoviruses HPV16L1ΔCE7 1–x were transfected by cotransfection of 10 μg of the recombinant plasmids and 2 μg of linearized Baculo-Gold DNA (Pharmingen, San Diego, Calif.) into Sf9 cells. Recombinant viruses were purified according to the instructions of the manufacturer. In order to test the expression, $10^6$ Sf9 cells were infected with recombinant Baculovirus and an m.o.i. (multiplicity of infection) of 5 to 10. After the incubation, the medium was removed and the cells washed with PBS (140 mM NaCl, 2.7 mM Kcl [sic], 8.1 mM $Na_2PO_4$, 1.5 mM $KH_2PO_4$, pH 7.2). The cells were then lysed in SDS sample buffer and tested by SDS gel chromatography and immunoblot assay.

3. Purification of Virus-like Particles

For the preparation of CVLPs, *Trichoplusia ni* (TN) High Five cells were cultured at 27° C. up to a density of 1–1.5×$10^6$ cells per ml in Ex-Cell 405 serum-free medium (JRH, Biosciences, Lennexa, Kans.). A 400 ml culture was harvested and infected with an m.o.i. of 2 to 5 with recombinant baculoviruses for one hour with periodic inversions. Up to 240 ml of medium were added and the cells grew for 3 to 4 days. The cells were then pelleted and resuspended in 10 ml of extraction buffer (10 mM $MgCl_2$, 1–50 mM $CaCl_2$, 150 mM NaCl, 20 mM Hepes, 0.01% Triton (optional), pH 7.4) and sonicated for 45 seconds at 60 watts. After centrifugation at 10,000 rpm in a Sorvall SS34 rotor, the pellet was dissolved in 6 ml of extraction buffer, sonicated for 30 seconds at 60 watts and centrifuged again. The supernatants were combined and applied to a two-stage gradient of 40% (w/v) succhrose and 57.5% (w/v) CsCl. After centrifugation in an SW-28 rotor at 27,000 rpm for two hours, the interphase and the CsCl layer were collected, adjusted to a CsCl density of 1.38 g/ml and centrifuged at 45,000 rpm for 16 hours. The gradients were fractionated and each fraction was tested by Western Plot using anti-HPV16L1mAb Camvir1 (Phamingen, San Diego, Calif.). The reactive fractions were combined and dialysed by means of an ultrafiltration using a Centricon 30 micro-concentrator (Amicon Corp. Beverly, Mass.) against Hepes buffer (1 mM Hepes, 149 mM NaCl, 0.5 mM KCl, pH 7.2) and the presence of CVLPs was confirmed by means of transmission electron microscopy. The concentration of L1E7 protein was determined approximately, in an SDS gel which was stained with Coomassie blue, by comparison with BSA standards.

4. Culturing of Mouse Cells

The C57BL/6-derived mouse cells TC-1 are primary pulmonary epithelial cells of C57BL/6 mice, which have been transformed by transfection with the oncogenes HPV-16 E6 and E7 and c-Ha-ras (Lin, K.-Y. (1996), supra). RMA (Ljungrenn & Karre (1985) J. Exp. Med., 162, 1745–1757) and the processing-defective cell line RMA-S are C57BL/6 thymoma cells. The HPV-16 E7-transfected RMA-E7 is described in Speidel, K. et al. (1997) Eur. J. Immunol., 27(9), 2391–2399. All cells were cultured in RPMI-1640, supplemented with 10% FCS, 2-ME, L-glutamine and antibiotics. 0.8 mg/ml of G418 (Gibco BRL, Gaithersburg, Md.) was added for the culturing of RMA-E7 transfectants. TC-1 cells additionally grew in the presence of 0.4 mg/ml of G418, 0.2 mg/ml of hygromycin and 1 mM sodium pyruvate.

5. Production of Cytotoxic T-cell (CTL) Lines

10–14 days after immunization, the spleen cells were prepared; 2–4×$10^7$ spleen cells were cocultured with $10^5$ irradiated (200 Gy) syngenic RMA-E7 transfectants per ml. After 5 days, the first $^{51}$Cr-release cytotoxicity test was carried out. For the production of CTL lines, the spleen cells were restimulated weekly in 24-hole plates with 2×$10^5$ irradiated RMA-E7 transfectants per hole as stimulator cells and 5×$10^6$ irradiated (33 Gy) C57BL/6 spleen cells per hole as feeder cells.

6. $^{51}$Cr-Release Cytotoxicity Test

For the $^{51}$Cr-release cytotoxicity test, effector T cells were added to 1×$10^4$ $^{51}$Cr-labelled target cells per hole on a 96-hole plate having a different effector cell to target cell ratio (E:T). The target cells were labelled with $Na_2^{51}CrO_4$ (100 μCi per 2×$10^6$ cells) for one hour at 37° C. The peptide having the sequence RAHYNIVTF (amino acid 49–57 of HPV-16 E7; Feltkamp, M. C. W. et al. (1993), Eur. J. Immunol., 23, 2242–2249) was added during this incubation in a concentration of 50 μM. In the peptide titration test with a constant E:T ratio, the $^{51}$Cr-labelled target cells were cultured with decreasing peptide concentrations (1 μg–100 pg per ml) for one hour at 37° C. before the effector cells were added. After incubation at 37° C. for four hours, 50 μl of the supernatant per hole were transferred to a Luma plate (Packard) and dried. The radioactivity was measured in a β-counter (Trilux Microbeta, Wallac). The mean specific lysis was calculated according to the following formula: % specific lysis=(experimental release−spontaneous release)/ (complete release−spontaneous release)×100.

7. Induction of E7-Specific Cytotoxic T Lymphocytes by CVLPs 11 six to sixteen week-old female C57BL/6 mice were immunized with 1–20 μg of CVLPs without adjuvant by means of a simple s.c. injection. Two weeks later, the spleen cells were prepared and stimulated in vitro with HPV-16 E7-expressing transfectants of the C57BL/6-derived tumour cell line RMA (RMA-E7) as stimulator cells. After culturing for five days, the first cytotoxicity test was carried out.

Figure 1:
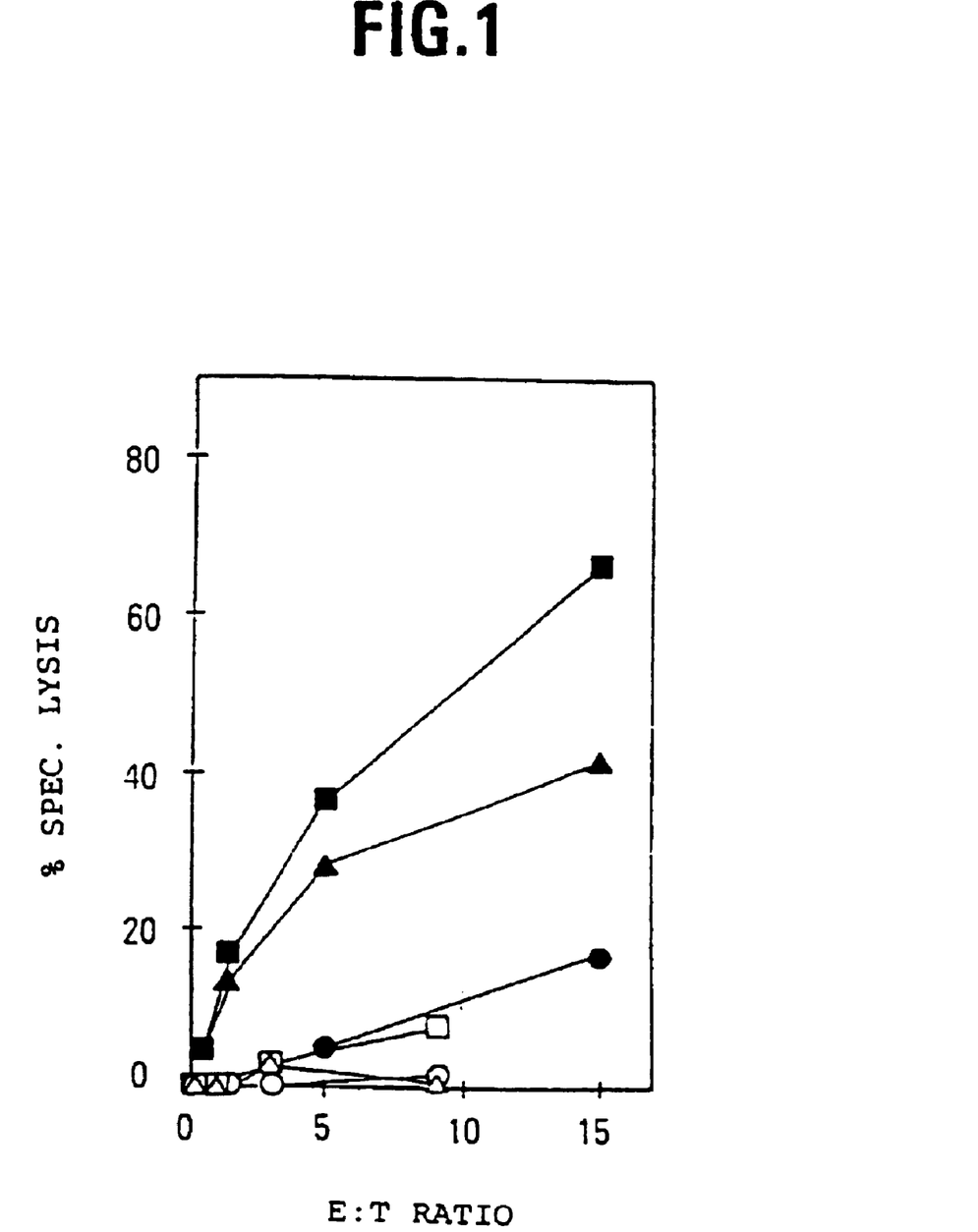
FIG. 1 shows an E7-specific CTL response which were produced after immunization with 1 µg of L1E7$_{1-60}$ CVLPs. The isolated spleen cells of mice immunized with L1E7$_{1-60}$ CVLPs (filled symbols) and HBS buffer (open symbols) were stimulated once in vitro with irradiated RMA-E7 cells and tested after five days in a standard four-hour $^{51}$Cr release cytotoxicity test with the following target cells: RMA-E7 cells (squares), E7$_{49-57}$ peptide-loaded RMA cells (triangular) and RMA cells (circles). The results are expressed as specific lysis in %.

The stimulation of the spleen cells was repeated at weekly intervals. As shown in FIG. 1, immunization with 1 μg of L1ΔCE7$_{1-60}$ CVLPs, i.e. the carboxy-terminal 34 amino acids of HPV-16 L1 were replaced by the amino acids 1–60 of HPV-16 E7, led to a strong E7-specific CTL response.

Altogether, after five days a specific lysis of RMA-E7 transfectants of between 7.7% and 54.7% (average value 33.6%; E:T ratio 8:1–33:1) was observed. The average lysis after the second stimulation was between 35.8% and 57.8% (average value 45.3%; E:T ratio 8:1–44:1). If the mice were only immunized with 1 μg of L1ΔCE$_{1-60}$ CVLPs, on average, after a culturing time of 5 days, a lower reactivity of E7-specific CTLs was observed (7.7–49.5%; average value 28.5%) than after immunization with 5 μg (17.2–44.7%; average value 33.9%) or 20 μg (26.0–54.7%; average value 38.5). The spleen cells of the control mice (vaccinated with HBS buffer) showed no E7-specific reactivity after five days (0.3–8.9%, average value 3.4%, E:T ratio 4:1–9:1).

Figure 2:
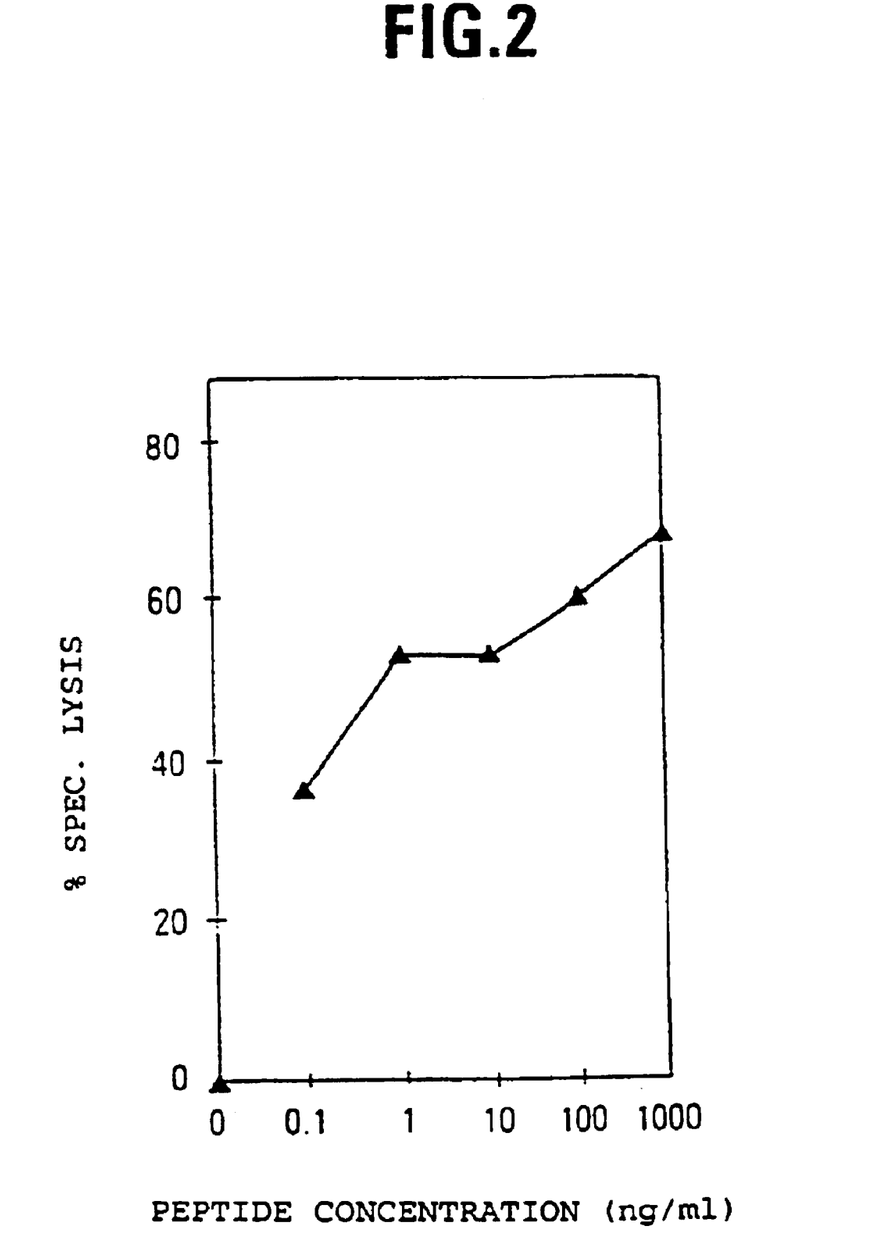
FIG. 2 shows the result of a titration test, carried out using an E7-specific CTL line which was obtained after vaccination of a C57BL/6 mouse with 20 µg of L1E7$_{1-60}$ CVLPs and in vitro stimulation three times with RMA-E7 transfectants. The peptide concentration was between 100 pg and 1 µg/ml. The target cells used were $^{51}$Cr-labelled E7 49–57 peptide-loaded RMA cells. The ratio of cells to target cells was 30:1.

L1ΔCE7$_{1-60}$ CVLP contains a known H2-D$^b$ T-cell epitope of the E7 protein (E7$_{49-57}$, Feltkamp, M. C. W. et al. (1993), supra). In order to confirm the obtained E7 specificity of the CTLs, they were therefore tested against RMA cells which are loaded with the peptide E7$_{49-57}$. CTLs which recognize RMA-E7 transfectants showed a specific cytotoxic activity against E7$_{49-57}$ RMA or RMA-S target cells. The measured specific lysis varied between 21.2–25% after five days (E:T ratio 8:1–15:1, see FIG. 1). In the peptide titration test carried out, after the third stimulation RMA-S cells were lysed to 70.5% or 71.4% (two CR lines were tested) after loading with E7$_{49-57}$ at a concentration of 1 μg/ml (E:T ratio 40:1, see FIG. 2). Even if RMA-S cells were provided with as little as 100 pg per ml of E7$_{49-57}$ peptide, a specific lysis of 36.2% and 47.2% was obtained. CTLs which are loaded with a control peptide, i.e. the influenza virus nucleoprotein-derived peptide having the amino acids 366–374, which represent a D$^b$-CTL epitope, were not recognized. Spleen cells which were isolated from C57BL/6mice after treatment with L1ΔCE7$_{1-55}$ CVLPs (E7 sequence truncated by five amino acids), did not recognize RMA-E7 cells, even if the mice were vaccinated with an increasing dose of up to 250 μg.

From these data, it is concluded that the CTLs were induced by L1ΔCE7$_{1-60}$ CVLPs, are E7-specific and recognize the peptide E7$_{49-57}$ with high affinity. In an FACS analysis of representative CTL lines, the CTLs were identified as CD8-positive.

8. Prevention of the Growth of a Syngenic E7-Expressing Tumour in C57BL/6 Mice In order to determine whether the vaccination with L1ΔCE7$_{1-60}$ CVLPs induce an effective immunity against syngeneic tumour cells (TC-1, Lin, K-Y. (1996), Cancer Res. 56, 21–26), tumour protection experiments were carried out. C57BL/6 mice (3–5 per group) received 1 s.c. injection of 10 μg of L1ΔCE7$_{1-60}$ CVLPs, 10 μg of L1ΔCE7$_{1-55}$ CVLPs, 10 μg of L1ΔC VLPs or an equivalent volume of HBS buffer without adjuvant. Two weeks after the immunization, 6×10$^4$ TC-1 cells, suspended in 200 μl of PBS, were inoculated into the left flank of the mice. The tumour size was measured twice per week for 2 months until the mice were killed.

Figure 3:
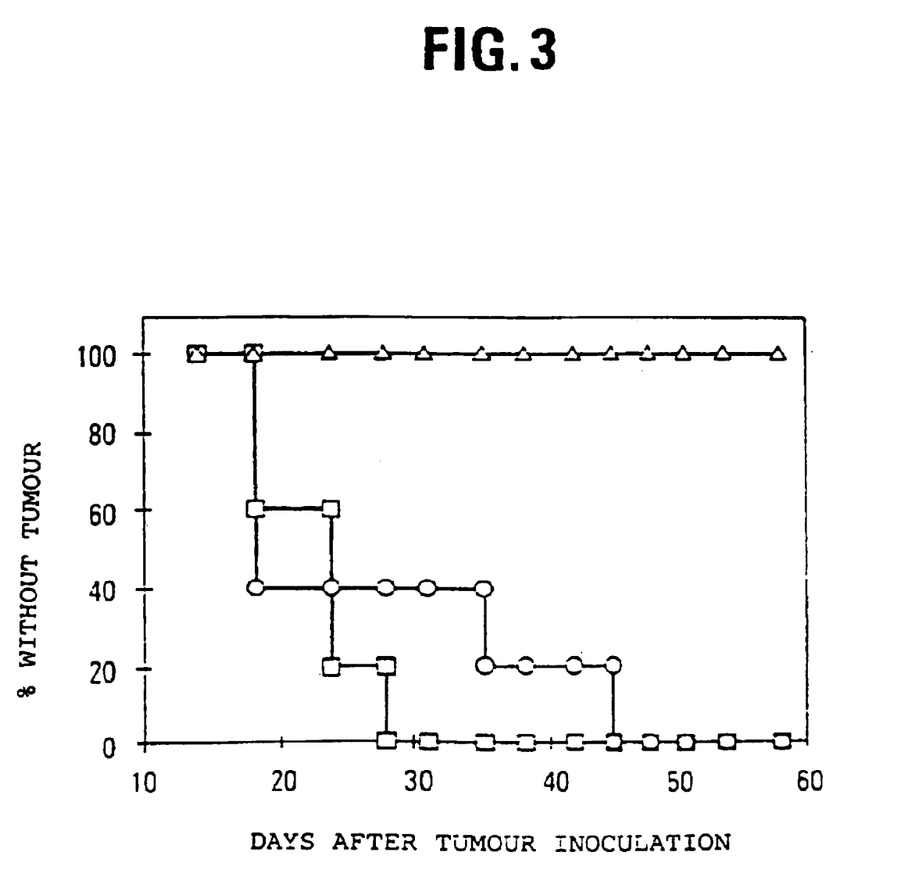
FIG. 3 shows the protection of C57BL/6 mice against the growth of TC-1 tumour cells. The mice (5 per group) were immunized s.c. either with 10 µg of L1E7$_{1-60}$ CVLPs (triangular), with 10 µg of L1ΔC VLPs (circles) or with HBS buffer (squares). Two weeks later, 6×10$^4$ TC-1 tumour cells per mouse were inoculated into the left flank of the mice s.c. The mice were checked twice per week.

The results of all experiments are summarized in Table 1. The total tumour growth rate in the mice which were vaccinated with HBS buffer, L1ΔC VLPs or L1ΔCE7$_{1-55}$ CVLPs was on average 80.5%. Vaccination with L1ΔC CVLPs did not protect against the tumour, although delayed tumour growth was observed (see FIG. 3). However, vaccination of mice with L1ΔCE7$_{1-60}$ CVLPs protected against tumour growth: only one mouse (1/13) developed a small, slowly growing tumour after 38 days, which regressed within a two-month period.

Spleen cells of HBS or L1ΔC VLP-vaccinated mice which developed TC-1 tumours showed no or only small levels of an E7-specific CTL response, independently of whether the mice had developed tumours or not. After the 2nd stimulation, an E7-specific lysis of RMA-E7 target cells of between 0–21% in tumour-bearing mice (average value 14%, E:T ratio 5:1–24:1), and of between 0 and 22.2% (average value 10.4%, E:T ratio 7:1–40:1), was observed in tumour-free mice. In contrast to this, in mice which were protected against tumour growth after the immunization with CVLP L1ΔCE7$_{1-60}$, an E7-specific CTL response of between 29.1 and 49.8% (average value 36.9%, E:T ratio 11:1–24:1) was found after the 2nd stimulation.

Figure 4:
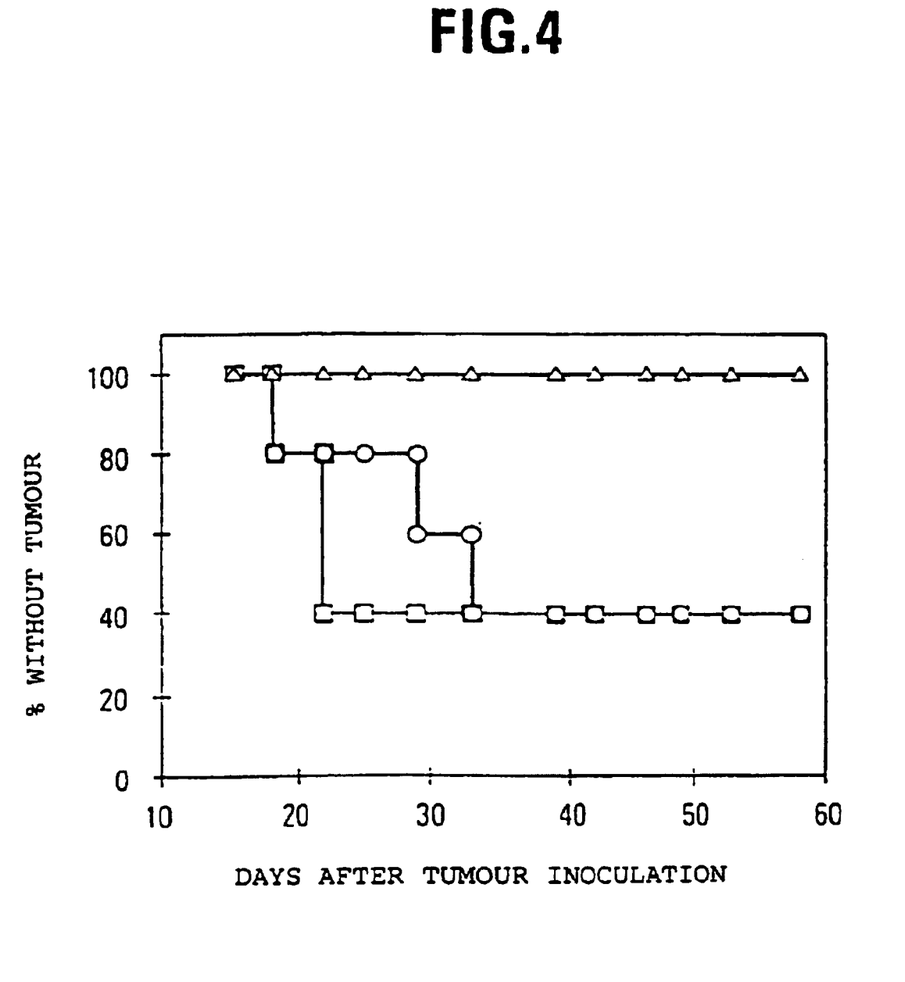
FIG. 4 shows the prevention of the growth of TC-1 tumour by L1E7$_{1-60}$ CVLPs. 6×10$^4$ TC-1 tumour cells per mouse were inoculated into the left flank of C57BL/6 mice (5 per group). Two weeks later, the mice were immunized with an s.c. injection of 10 µg of L1E7$_{1-60}$ CVLPs (triangles), 10 µg of L1ΔCVLPs (circles) or HBS buffer (squares).
Figure 5:
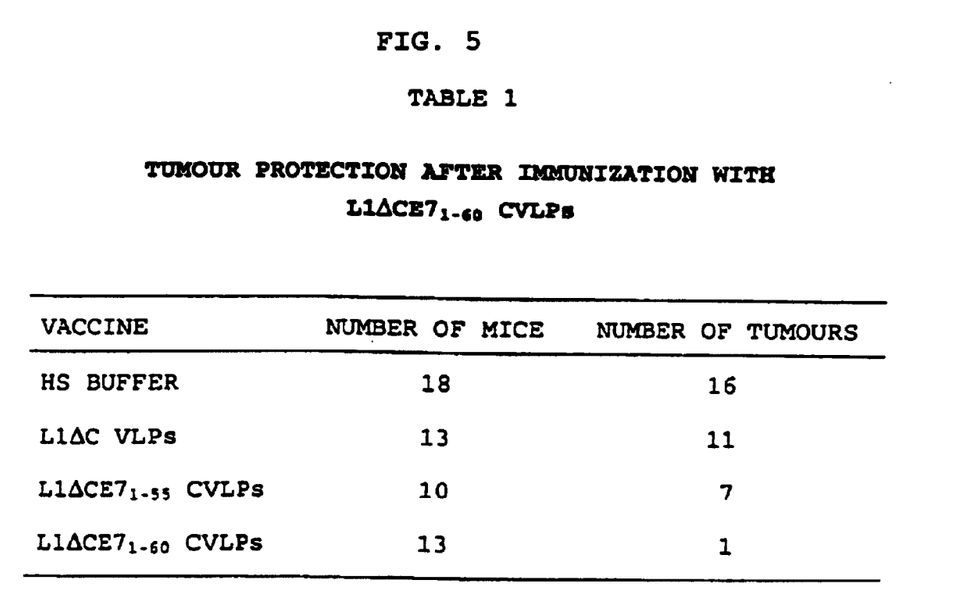
FIG. 5 shows tumor protection in C57BL16 mice by L1 ΔCE7$_{1-60}$CVLPs. Two weeks after innoculation of 6×10$^4$ TC-1 cells, the mice received a single injection of L1 ΔCE7$_{1-60}$CVLPs. The mice were analyzed for the presence of tumors.

It was furthermore analysed whether the vaccination leads to a regression of already existing tumours. Two weeks after the inoculation of 6×10$^4$ TC-1 cells (s.c.), the mice (5 per group) received a single injection of 10 μg of L1ΔCE7$_{1-60}$ CVLPs, 10 μg of VLP L1ΔC or HBS buffer without adjuvant. In this experiment (see FIG. 4), the tumour development of control mice which were either treated with HBS or immunized with VLP L1ΔC was only 60% (3 of each group, 6/10). However, all mice (5/5) which were vaccinated with L1ΔCE7$_{1-60}$ CVLPs generated an immune response against the established tumours and remained tumour-free two months after the tumour cell injection.

It will be apparent to those skilled in the art that various modifications and variations can be made to the compositions and processes of this invention. Thus, it is intended that the present invention cover such modifications and variations, provided they come within the scope of the appended claims and their equivalents.

Priority application DE 198 12 941.6, filed Mar. 24, 1998, including the specification, drawings, claims and abstract, is hereby incorporated by reference. All publications cited herein are incorporated in their entireties by reference.

We claim:

1. A pharmaceutical composition comprising at least one HPV 16 L1ΔE7$_{1-55}$ fusion protein, wherein the fusion protein contains no papillomavirus-unspecific epitopes and wherein the pharmaceutical composition is capable of treating human papillomavirus (HPV)-specific tumour.

2. The pharmaceutical composition according to claim 1, wherein the fusion protein is present in the form of a capsid and/or capsomer.

3. The pharmaceutical composition according to claim 1, wherein the tumour is a carcinoma of the larynx, cervix, penis, vulva or anus.

4. The pharmaceutical composition according to claim 1, wherein the pharmaceutical composition contains no adjuvant.

5. The pharmaceutical composition according to claim 1, wherein the pharmaceutical composition comprises suitable additives and/or excipients.

6. The pharmaceutical composition according to claim 5, wherein the additive or excipient is about 0.3 to about 4 M of a salt having a pH of about 7.3 to about 7.45.

7. The pharmaceutical composition according to claim 6, wherein the additive or excipient is 0.4 to about 3 M of a salt having a pH of about 7.3 to about 7.45.

8. The pharmaceutical composition according to claim 6, wherein the additive or excipient is 0.5 to about 2 M of a salt having a pH of about 7.3 to about 7.45.

9. The pharmaceutical composition according to claim 6, wherein the additive or excipient is 1 to about 2 M of a salt having a pH of about 7.3 to about 7.45.

10. The pharmaceutical composition according to claim 6, wherein the salt has a pH of 7.4.

11. The pharmaceutical composition according to claim 6, wherein the salt is an alkali metal or alkaline earth metal salt.

12. The pharmaceutical composition according to claim 11, wherein the salt is a halide or a phosphate.

13. The pharmaceutical composition according to claim 11, wherein the salt is an alkali metal halide.

14. The pharmaceutical composition according to claim 11, wherein the salt is NaCl and/or KCl.

15. The pharmaceutical composition according to claim 6, wherein the pH is adjusted using a buffer.

16. The pharmaceutical composition according to claim 15, wherein the pH is adjusted using a phosphate buffer, tris buffer, HEPES buffer or MOPS buffer.

17. A method for producing a pharmaceutical composition comprising combining at least one HPV 16 L1ΔE7$_{1-55}$ fusion protein of claim 1 together with one or more pharmaceutically acceptable excipients to form a pharmaceutical composition, said pharmaceutical composition being capable of treating human papillomavirus (HPV)-specific tumour.

18. A method for treating human papillomavirus (HPV)-specific tumour, comprising administering to a subject in need thereof a pharmaceutical composition according to claim 1.

* * * * *

SEQUENCE LISTING

<160> NUMBER OF SEQ ID NOS: 12

<210> SEQ ID NO 1
<211> LENGTH: 40
<212> TYPE: DNA
<213> ORGANISM: artificial sequence
<220> FEATURE:

-continued

```
<223> OTHER INFORMATION: Oligonucleotide PCR-primer that introduces a
      restriction site

<400> SEQUENCE: 1
aaagatatct tgtagtaaaa atttgcgtcc taaaggaaac                              40

<210> SEQ ID NO 2
<211> LENGTH: 44
<212> TYPE: DNA
<213> ORGANISM: artificial sequence
<220> FEATURE:
<223> OTHER INFORMATION: Oligonucleotide PCR-primer that introduces a
      restriction site

<400> SEQUENCE: 2
aaagatatct aatctacctc tacaactgct aaacgcaaaa aacg                        44

<210> SEQ ID NO 3
<211> LENGTH: 35
<212> TYPE: DNA
<213> ORGANISM: artificial sequence
<220> FEATURE:
<223> OTHER INFORMATION: Oligonucleotide PCR-primer that introduces a
      restriction site

<400> SEQUENCE: 3
aaaagatatc atgcatggag atacacctac attgc                                  35

<210> SEQ ID NO 4
<211> LENGTH: 34
<212> TYPE: DNA
<213> ORGANISM: artificial sequence
<220> FEATURE:
<223> OTHER INFORMATION: Oligonucleotide PCR-primer that introduces a
      restriction site

<400> SEQUENCE: 4
ttttgatatc ggctctgtcc ggttctgctt gtcc                                   34

<210> SEQ ID NO 5
<211> LENGTH: 24
<212> TYPE: DNA
<213> ORGANISM: artificial sequence
<220> FEATURE:
<223> OTHER INFORMATION: Oligonucleotide primer for "Four primer PCR"

<400> SEQUENCE: 5
gttatgacat acatacattc tatg                                              24

<210> SEQ ID NO 6
<211> LENGTH: 35
<212> TYPE: DNA
<213> ORGANISM: artificial sequence
<220> FEATURE:
<223> OTHER INFORMATION: Oligonucleotide primer for "Four primer PCR"

<400> SEQUENCE: 6
ccatgcattc ctgcttgtag taaaaatttg cgtcc                                  35

<210> SEQ ID NO 7
<211> LENGTH: 29
<212> TYPE: DNA
<213> ORGANISM: artificial sequence
<220> FEATURE:
<223> OTHER INFORMATION: Oligonucleotide primer for "Four primer PCR"

<400> SEQUENCE: 7
```
ctacaagcag gaatgcatgg agatacacc                                   29

<210> SEQ ID NO 8
<211> LENGTH: 36
<212> TYPE: DNA
<213> ORGANISM: artificial sequence
<220> FEATURE:
<223> OTHER INFORMATION: Oligonucleotide primer for "Four primer PCR"

<400> SEQUENCE: 8
catctgaagc ttagtaatgg gctctgtccg gttctg                           36

<210> SEQ ID NO 9
<211> LENGTH: 38
<212> TYPE: DNA
<213> ORGANISM: artificial sequence
<220> FEATURE:
<223> OTHER INFORMATION: Oligonucleotide PCR-primer that introduces
      three additional codons for a C-terminal extension of the coded
      fusion protein

<400> SEQUENCE: 9
catctgaagc ttatcaatat tgtaatgggc tctgtccg                         38

<210> SEQ ID NO 10
<211> LENGTH: 54
<212> TYPE: DNA
<213> ORGANISM: artificial sequence
<220> FEATURE:
<223> OTHER INFORMATION: Oligonucleotide PCR-primer that introduces
      eight additional codons for a C-terminal extension of the coded
      fusion protein

<400> SEQUENCE: 10
catctgaagc ttacttgcaa caaaaggtta caatattgta atgggctctg tccg       54

<210> SEQ ID NO 11
<211> LENGTH: 69
<212> TYPE: DNA
<213> ORGANISM: artificial sequence
<220> FEATURE:
<223> OTHER INFORMATION: Oligonucleotide PCR-primer that introduces
      thirteen additional codons for a C-terminal extension of the
      coded fusion protein

<400> SEQUENCE: 11
catctgaagc ttaaagcgta gagtcacact tgcaacaaaa ggttacaata            50
ttgtaatggg ctctgtccg                                              69

<210> SEQ ID NO 12
<211> LENGTH: 47
<212> TYPE: DNA
<213> ORGANISM: artificial sequence
<220> FEATURE:
<223> OTHER INFORMATION: Oligonucleotide PCR-primer that introduces
      eight additional codons for a C-terminal extension of the coded
      fusion protein

<400> SEQUENCE: 12
catctgaagc ttattgtacg cacaaccgaa gcgtagagtc acacttg                47